United States Patent [19]
Gindler

[11] 3,953,359
[45] Apr. 27, 1976

[54] DETERMINATION OF PHOSPHORUS
[75] Inventor: E. Melvin Gindler, Rockford, Ill.
[73] Assignee: Pierce Chemical Company, Rockford, Ill.
[22] Filed: Apr. 23, 1974
[21] Appl. No.: 463,405

[52] U.S. Cl. ............................. 252/408; 23/230 B; 424/7
[51] Int. Cl.² ................... G01N 31/22; G01N 33/16
[58] Field of Search ............... 23/230 B; 252/408; 424/1, 7, 12; 195/103.5

[56] References Cited
UNITED STATES PATENTS
3,823,094  7/1974  Lancz .................................. 252/527
3,853,465  12/1974  Rush et al. ......................... 23/230 B
3,853,469  12/1974  Morin .............................. 23/230 B OTHER PUBLICATIONS
McCutcheons: Detergents and Emulsifiers, Allured Publishing Corp., 1970, pp. 106–107.

Primary Examiner—Leland A. Sebastian
Assistant Examiner—David Leland

[57] ABSTRACT

A one step method for the spectrophotometric determination of phosphorus in the presence of protein using molybdic acid is disclosed. Protein precipitation is avoided by including a long chain amine ethylene oxide adduct in the sample reagent mixture being analyzed.

17 Claims, No Drawings

DETERMINATION OF PHOSPHORUS

The present invention relates to the quantitative determination of inorganic phosphorus and, more particularly, to the determination of phosphorus in biologic fluids which can contain proteins. The invention is especially concerned with a one step procedure for determining phosphorus concentration in human sera without the necessity for removing protein.

The use of molybdic acid to spectrophotometrically determine phosphorus concentration has been employed for many years (see Reviews of R. G. Henry, Clinical Chemistry, Principals and Techniques, Harper and Row, New York, 1964, pp. 409–411, and R. J. Martinek, J. Am. Med. Technol, 32, 337 (1970)). The procedure generally involves adding to the sample to be analyzed a molybdate salt such as ammonium molybdate, an acid such as sulphuric acid to form molybdic acid, and a reducing agent such as p-methylammonium phenol sulphate. Under acidic conditions the molybdic acid complexes with inorganic phosphate to form phosphomolybdate which is then reduced (probably M. (VI) to Mo (V)) to give the characteristic molybdenum blue color. The color intensity can be used to indicate the concentration of the phosphomolybdate complex, and, in turn, the concentration of phosphorus in the sample. Acidic conditions are necessary to obtain the phosphomolybdate complex and to subsequently reduce molybdenum.

The problem encountered is that under acidic conditions molybdic acid and phosphomolybdate precipitate protein resulting in undesirable turbidity of the sample being analyzed. This problem is further magnified when other protein precipitating reagents such as cupric sulphate are present. As is recognized, the cupric ion speeds formation of the molybdenum blue complex and is, therefore, desirably present (Delsal and Manhouri, Bull. Soc. Chim. Biol. (Paris) 40, 623 (1958), given in Wootton, Micro-Analysis in Medical Biochemistry, 4th Ed., Churchill Ltd., London, England, 1964, (pp. 77-78).

In order to avoid protein precipitation, deproteinization of the sample being analyzed has been accomplished. Such has been done by adding trichloroacetic acid to the sample to precipitate proteins which are then removed by centrifugation or filtration. This, however, involves an undesirable pretreatment step and also the precipitate usually contains part of the phosphate sought to be determined. Other deproteinization techniques such as dialysis have also been employed.

Another technique for eliminating the adverse influence of protein involves solubilizing precipitated protein after formation of the molybdenum blue complex. Such solubilization can be simply effected by adding an alkaline solution to the sample after formation of the blue complex. Raabe, Rec. Trav. Chim. Pays — Bas 74, 652 (1955), Richterich, Klinische Chemie Theorie und Praxis, Basel, Switzerland and New York, N.Y. (1968), and Meulemans, Clin, Chim. Acta 6, 145-6, (1961)). Such procedures, of course, are necessarily "two-step" in nature since the system must initially be acidic in order to form the desired phosphomolybdic complex and thereafter rendered alkaline in order to solubilize the protein. Certain improvements on these procedures have been described by Denney and Denney, U.S. Pat. No. 3,547,586, and Gindler and Ishizaki, Clin. Chem. 15,807 (1969) wherein protective colloids such as polyvinyl pyrrolidone and ethylene oxide adducts have been employed.

As is apparent, procedures wherein either protein is removed prior to sample analysis or wherein protein is solubilized in a separate step are time consuming. The advantage of a one step procedure obviating the necessity for protein removal or resolubilization is thus evident. As far as is presently known, only Hycel Corporation and Harleco provide one step phosphorus reagent procedures. A one step procedure is described by Morin and Prox, Clin. Chim. Acta 46, 113-7 (1973). Also see U.S. Pat. No. 3,853,469.

Accordingly, it is a principal object of the present invention to provide a one step procedure for spectrophotometrically determining phosphorus concentration. And, related thereto is the objective of providing a method for determining phosphorus concentration which obviates the necessity of either using a protein free sample or solubilizing a protein precipitate.

An additional object resides in providing a one step phosphorus procedure which utilizes the well recognized phosphomolybdate technique but in which protein precipitation is avoided.

A further object is to provide a procedure having the above identified attributes wherein cupric ion can also be present in order to accelerate the procedure.

Yet a further object resides in providing a reagent composition which can be effectively utilized in the one step spectrophotometric determination of phosphorus.

Other objectives and advantages of the present invention will become apparent in view of the following description.

Briefly stated, the present invention is based on the discovery that certain long chain amine ethyleneoxide adducts and their quaternized derivatives can be used to effectively prevent precipitation of proteins by molybdic acid and/or the phosphomolybdate complex. These adducts are further characterized as being water soluble compounds which are cationic in acid solution and which contain lipophilic and hydrophilic nonionic groups.

In acid solution, these compounds are present in the form of cationic ammonium salts. It is believed that, due to their cationic and lipophilic character, these salts complex with the molybdenum compounds present and possibly also protein. The polyether groups of the compound, being hydrophilic, keep the resulting complexed structure in solution and thus precipitate formation is avoided.

Particularly useful compounds of this type can be generally represented by the following formula:

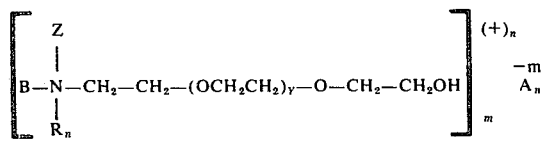

wherein:

$A^{-m}$ is a non-interfering anion, i.e. an anion which does not effectively compete with phosphorus for molybdenum or does not promote interference with the molybdenum blue color, with m being 1, 2, or more;

B is a lipophilic group containing about 6–28 carbon atoms, preferably 14–22 carbon atoms;

Z is H or $-CH_2-CH_2-(OCH_2CH_2)_x-O-CH_2-CH_2OH$;

R is H or a lipophilic group containing about 1–10 carbon atoms, preferably $CH_3$;

X and Y are integers with the sum of X and Y being 5–30, preferably 5–20 with the integers X and Y being about the same; and n is 0 or 1.

Referring to the foregoing formula, it should be appreciated that quaternized compounds are represented when n is 1. And, in this case, the non-interfering anion $A^{-m}$ is preferably $Cl^-$, $SO_2^=$, or $CH_3$-$O$-$SO_3^-$. Similar anions can also be used such as other halogens, e.g., $Br^-$, $F^-$, other alkoxy sulfites, and polycarboxylates of low molecular weight. However, the use of arsenates, phosphates and the like which can react with molybdenum should, of course, be avoided.

As to the lipophilic groups B and R, these cannot have a chain length which prevents the adduct from being water soluble. Thus, B should not have a carbon atom content in excess of about 28 carbon atoms and, when the adduct is quaternized (n is 1), the carbon atom content of R does not exceed about 10. The lipophilic groups are preferably saturated hydrocarbons, e.g., straight or branched alkyls, though aryl, alkylaryl and cycloaliphatic containing groups are also useful. Similarly, so long as the group remains lipophilic, it can contain substituents such as halogens or contain ether or thioether units.

Lastly, the presence of ethyleneoxide in the compound is important in order to provide hydrophilic functionality. However, so as not to adversely affect the combined lipophilic hydrophilic character of the adduct, the content of ethyleneoxide should not exceed that given above. Preferably, the group Z in the above formula is a polyethylene oxide with X being about the same as Y.

The preparation of the adducts useful herein is conventional and can involve the initial preparation of a long chain amine by, for example, reaction of ammonia with an acid ester to give an amide which can be then reduced to the corresponding amine. The adduct is then prepared by reacting the amine with ethylene oxide in known fashion. When the quaternized derivative is desired (n in the above formula being one), the ethoxylated amine can be simply reacted with an alkylating agent, e.g. methyl chloride or the like. Useful adducts and their quaternized derivatives are offered commercially by Armark Corporation under the tradenames "Ethomeen" and "Ethoquad," respectively.

The amount of adduct employed is not particularly critical so long as a sufficient amount is used to prevent protein precipitation. Simple experimentation can be employed to determine the appropriate amount to be used. In general, based on 100 microliters of sample being analyzed, the adduct should be present in an amount of at least about 25 milligrams and ordinarily not in excess of about 155 milligrams.

The following example illustrates the present invention. All parts and percentages are by weight unless otherwise indicated.

Four liters of aqueous solution were prepared by addition of the following ingredients to deionized water:

150 gm. "Ethoquad" 18/25 quaternized hydrocarbon amine ethyleneoxide adduct. (Re above formula: R is methyl, B is linear saturated aliphatic having about 18 carbon atoms, Z is polyethylene oxide group with compound containing about 15 moles ethylene oxide, A is Cl, $m$ and $n$ being 1).

100 ml. $CH_3COOH$ } buffer to give pH of about 3
40 gm. $CH_3COONa.3H_2O$ 20 gm. $(CH_3NH_2-\langle\bigcirc\rangle-OH)_2SO_4$ (reducing agent)

40 gm. $Na_2S_2O_5$ (to protect reducing agent from decomposing and also functions as reducing agent.)

500 ml. of a second aqueous solution were prepared by addition of the following ingredients to deionized water:

5 gm. $(NH_4)_6Mo_7O_{24}.7H_2O$ 3 gm. $CuSO_4.5H_2O$ 6 ml. conc. $H_2SO_4$ (prevents Mo-Cu precipitate)

A working reagent is then prepared by mixing ten volumes of the first of the above-identified solutions with one volume of the second solution. The working reagent is stable for at least about four hours at room temperature. Three milliliters of the working reagent are then combined with 0.100 milliliter (100 microliters) of the sample to be analyzed, e.g., sera, urine, etc. The resulting solution is allowed to stand for about 30 minutes, after which time the characteristic molybdenum blue color is substantially fully developed. The absorbence of the solution is then read at about 660–700 nm, preferably 690 nm using a blank of 100 microliters water and 3 milliliters working reagent.

In a conventional fashion, a suitable calibration graph using samples of known phosphorus concentrations can be constructed for the purpose of quantitatively determining the amount of phosphorus in the unknown. The same time interval between addition of the working reagent and absorbency reading should be used for the calibration as was used for the unknown sample, though this is less critical with respect to intervals of 30 minutes or more. Beer's law is followed over a concentration range of about 0 to 10 mg. P/ml.

While the invention has been described in connection with certain preferred embodiments, it is to be understood that the invention is not to be limited to only those embodiments. On the contrary, it is intended to cover all modifications thereof falling within the spirit and scope of the invention as expressed in the appended claims. Thus whereas a specific working reagent has been described, it should be understood that the concentrations of the conventionally used ingredients therein specified can vary, e.g. ± 10%. Similarly different buffers, reducing agents, acids, copper salts, pH and the like can also be used so long as they do not adversely affect the determination of phosphorus in the manner indicated. In particular, mixtures of 3-butene-1, 4-diol and either O-phenylenediamine or 2,4-diaminophenol dihydrochloride, in about equal weight amounts, can be used as reducing agents in place of the specifically illustrated p-methyl ammonium phenol sulphate.

I claim as my invention:

1. In an aqueous solution useful for the spectrophotometric determination of inorganic phosphorus containing a reducing agent effective to reduce a phosphomolybdate complex to yield its characteristic blue color, the improvement wherein the solution also contains a water soluble long chain hydrocarbon amine ethyleneoxide adduct or quaternized derivative thereof which is cationic in acid solution and contains lipophilic and hydrophilic nonionic groups, said adduct or quaternized derivative thereof being present in an amount sufficient to prevent protein precipitation when said solution also contains protein, molybdic acid and a phosphomolybdate complex.

2. The aqueous solution of claim 1 wherein the water soluble long chain hydrocarbon amine ethylene oxide adduct or quaternized derivative thereof is represented by the following formula:

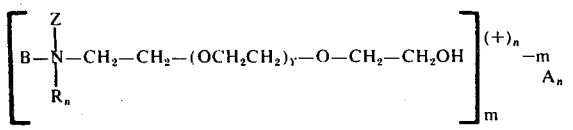

wherein $A^{-m}$ is a non-interfering anion which does not effectively compete with phosphorus for molybdenum or does not promote interference with the characteristic blue color of a phosphomolybdate complex with m being 1, 2 or more; B is a lipophilic group containing about 6–28 carbon atoms; Z is H or $-CH_2-CH_2-(OCH_2CH_2)_x-O-CH_2OH$; R is H or a lipophilic group containing about 1–10 carbon atoms; X and Y are integers with the sum of X and Y being 5–30, and n is 0 or 1.

3. The aqueous solution of claim 2 wherein $A^{-m}$ is $Cl^-$, $SO_2^=$, or $CH_3-O-SO_3^-$; B is a lipophilic group containing about 14–22 carbon atoms; Z is $-CH_2-CH_2-(OCH_2CH_2)_x-O-CH_2-CH_2OH$; X and Y are integers with sum of X and Y being 5–20.

4. The aqueous solution of claim 3 wherein $A^{-m}$ is $Cl^-$ and R is $CH_3$.

5. The aqueous solution of claim 4 wherein the integers X and Y are about the same.

6. The aqueous solution of claim 5 wherein n is 0.

7. The aqueous solution of claim 5 wherein n is 1.

8. The aqueous solution of claim 1 containing protein, molybdic acid and a phosphomolybdate complex.

9. In the spectrophotometric process for the determination of inorganic phosphate comprising complexing inorganic phosphate to be analyzed with molybdenum to form a phosphomolybdate complex, reducing the complex to give its characteristic blue color and spectrophotometrically measuring the color intensity of said reduced complex, the improvement wherein the spectrophotometric measurement of color intensity is effected in an aqueous solution which has included therein a water soluble long chain hydrocarbon amine ethylene oxide adduct or quaternized derivative thereof which is cationic in acid solution and contains lipophilic and hydrophilic nonionic groups, said adduct or quaternized derivative thereof being present in an amount sufficient to prevent protein precipitation in said aqueous solution.

10. The process of claim 9 wherein the water soluble long chain hydrocarbon amine ethylene oxide adduct or quaternized derivative thereof is represented by the following formula:

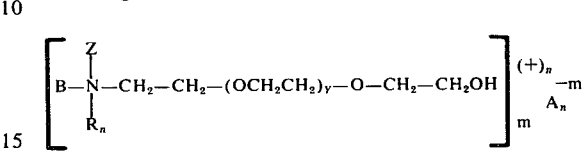

wherein $A^{-m}$ is a non-interfering anion which does not effectively compete with phosphorus for molybdenum or does not promote interference with the characteristic blue color of a phosphomolybdate complex with m being 1, 2 or more; B is a lipophilic group containing about 6–28 carbon atoms; Z is H or $-CH_2-CH_2-(OCH_2CH_2)_x-O-CH_2-CH_2OH$; R is H or a lipophilic group containing about 1–10 carbon atoms; X and Y are integers with the sum of X and Y beint 5–30, and n is 0 or 1.

11. The process of claim 10 wherein $A^{-m}$ is $Cl^-$, $SO_2^=$, or $CH_3-O-SO_3^-$; B is a lipophilic group containing about 14–22 carbon atoms; Z is $-CH_2-CH_2-(OCH_2CH_2)_x-O-CH_2-CH_2OH$; X and Y are integers with sum of X and Y being 5–20.

12. The process of claim 11 wherein $A^{-m}$ is $Cl^-$ and R is $CH_3$.

13. The process of claim 12 wherein the integers X and Y are about the same.

14. The process of claim 13 wherein n is 0.

15. The process of claim 13 wherein n is 1.

16. The aqueous solution of claim 5 wherein the reducing agent is para-methyl ammonium phenol sulfate.

17. The process of claim 13 wherein reduction of the complex is effected with para-methyl ammonium phenol sulfate.

* * * * *